(12) United States Patent
Brouse

(10) Patent No.: US 6,526,836 B1
(45) Date of Patent: Mar. 4, 2003

(54) BITUMINOUS PAVEMENT FATIGUE TESTING DEVICE

(75) Inventor: Gregory L. Brouse, Middleburg, PA (US)

(73) Assignee: Eastern Industries, Inc., Winfield, PA (US)

( * ) Notice: Subject to any disclaimer, the term of this patent is extended or adjusted under 35 U.S.C. 154(b) by 87 days.

(21) Appl. No.: 09/594,610

(22) Filed: Jun. 15, 2000

(51) Int. Cl.[7] ................................................. G01N 3/00
(52) U.S. Cl. .............................. 73/818; 73/813; 73/803; 73/790; 73/760
(58) Field of Search .......................... 73/813, 821, 818, 73/824, 825, 847, 851

(56) References Cited

U.S. PATENT DOCUMENTS

| | | |
|---|---|---|
| 1,457,015 A | 5/1923 | Besson |
| 2,637,198 A | 5/1953 | Spangler et al. |
| 2,892,342 A | 6/1959 | Goss et al. |
| 4,168,620 A | 9/1979 | Schrader |
| 4,412,448 A | 11/1983 | Flynn et al. |
| 5,911,164 A | * 6/1999 | McRae .......................... 73/815 |

OTHER PUBLICATIONS

Huber, Gerald A., "Development of the Superpave Gyratory Compactor", pp. 1–4, 1997.
Gyratory Testing Machine (GTM), pp. 1–2, 5/99.
Product Brochure on Troxler Gyratory Compactor, Troxler Electronic Laboratories, Inc., p. 1 (two–sided), Mar. 98.
Product Brochure on ITC Gyratory Compacator, Interlaken Technology Corporation, p. 1 (two–sided).
Product Brochure on Test Quip Brovold Gyratory AASHTO TP4, PP35; ASTM Pending; SHRP M–002, , p. E–36.
Product Brochure on Wheel Tracking Machine, BS 598 Part 110; prEN 12697–22, p. E–45.
Correlation Between Wheel Tracking and ALF Rutting, Polymer Modified Binder (PMB) Field Trials, pp. 1–4, Mar. 22, 1998.
Blankenship, Phil "Experiences with Superpave Volumetric Mix Designs" (KOCH Materials Co.), pp. 1–2, 1996.
Evaluation of Natural Sand Used in Asphalt Mixtures, Publication No. FHWA–RL–93–070, by Office Engineering and Highway Operations R&D, NTIS Publication No. PB93–217289, p. 5.

* cited by examiner

*Primary Examiner*—Benjamin R. Fuller
*Assistant Examiner*—Andre Allen
(74) *Attorney, Agent, or Firm*—Nixon & Vanderhye, P.C.

(57) ABSTRACT

A method and apparatus for analyzing bituminous concrete mixes to predict the likelihood of early rutting is disclosed. A test head designed to be used in a gyratory compactor uses the compaction provided by the gyratory compactor to analyze bituminous mixes to determine whether they are likely to prematurely rut. A test specimen of bituminous mix is prepared to a specified air void content and then heated to a constant temperature and placed in the gyratory compactor. The test head, which consists of a hard rubber block in the shape of a truncated cone mounted in the direct center of a flat, metal circular disk, is placed on top of the specimen in the gyratory compactor with the rubber head down and engaging the test specimen. Once compaction is completed, mix specimen compaction data is analyzed to ascertain the degree of mix deformation for a specified number of gyrations, to thereby predict whether the mix is likely to prematurely rut.

30 Claims, 5 Drawing Sheets

BITUMINOUS PAVEMENT FATIGUE TESTING DEVICE

FIELD OF THE INVENTION

The present invention relates to the testing of bituminous concrete (blacktop), and, in particular, to a method and apparatus for analyzing bituminous concrete mix to predict the probability of early rutting.

BACKGROUND OF THE INVENTION

Today, highways and other roads are constructed from bituminous concrete. Bituminous concrete, which is commonly referred to as blacktop, is typically formed from a mix of different size aggregate materials. Because the properties of bituminous concrete will vary depending on the mix of aggregates that are used (or even available) to make it, the ability of one mix to endure traffic volume will often vary from that of another mix.

Today's increased traffic volumes on highways and other roads require today's road pavements to be better designed and have a longer life so that traffic can move along such roads safely and with little delay. This demand for better designed road pavements has increased the need to better predict pavement performance to avoid the need to prematurely replace pavements that fail under high traffic volumes. One indicator of a pavement's ability to endure high traffic volumes is its ability to resist rutting caused by the traffic traveling over the pavement.

In more recent times, the demand for road pavements that are capable of enduring high traffic volumes has resulted in the development of what are known as Superpave mixes of blacktop. Superpave mixes are typically coarser mixes having better performance characteristics, vis-à-vis, rutting, fatigue cracking and low temperature cracking. Because the design of the aggregate mix used to make a Superpave mix can determine how a road paved from the mix will perform, there still exists the need to predict pavement performance with respect to a road's ability to endure high traffic volumes.

One tool that has been used in the design of pavement mixes is the gyratory compactor, a device used to compress specimens of blacktop mixes for the purpose of evaluating the rate of densification of the mix. Typically a blacktop mix will include large and small aggregates. The kneading action provided by the gyratory compactor allows a specimen of the blacktop mix to be compacted. The mix is normally compacted 75, 115, 160 or 205 gyrations depending on the specifications and traffic demands for a particular application, as shown in Table 1 below.

TABLE 1

Superpave Gyratory Compaction Effort

| Design ESALs[1] (million) | Compaction Parameters | | | Typical Roadway Application[2] |
|---|---|---|---|---|
| | $N_{initial}$ | $N_{design}$ | $N_{max}$ | |
| <0.3 | 6 | 50 | 75 | Applications include roadways with very light traffic volumes such as local roads, county roads, and city streets where truck traffic is prohibited or at a very minimal level. Traffic on these roadways would be considered local in nature, not regional, intrastate, or interstate. Special purpose roadways serving recreational sites or areas may also be applicable to this level. |
| 0.3 to <3 | 7 | 75 | 115 | Applications include many collector roads or access streets. Medium-trafficked city streets and the majority of county roadways may be applicable to this level. |
| 3 to <30 | 8 | 100 | 160 | Applications include many two-lane, multilane, divided, and partially or completely controlled access roadways. Among these are medium to highly trafficked city streets, many state routes, U.S. highways, and some rural interstates. |
| ≧30 | 9 | 125 | 205 | Applications include the vast majority of the US Interstate system, both rural and urban in nature. Special applications such as truck-weighing stations or truck-climbing lanes on two-lane roadways may also be applicable to this level. |

[1]Design ESALs are the anticipated project traffic level expected on the design lane over a 20-year period. Regardless of the actual design life of the roadway, determine the design ESALs for 20 years, and choose the appropriate $N_{design}$ level.
[2]Typical Roadway Applications as defined by "A Policy on Geometric Design of Highway and Streets", 1994, AASHTO.

After compacting the mixture, it is tested for density. A densification curve is calculated by comparing the specimen's density with height measurements that are automatically recorded throughout the compaction process. This densification curve is then analyzed for compliance with specified density criteria (See Table 2 below). If the air void content is less than 2.0% at the specified maximum number of gyrations, the mix is deemed to be unacceptable.

TABLE 2

Superpave HMA Design Requirements

| Design ESALs[1] (million) | Required Density (% of Theoretical Maximum Specific Gravity) | | | Voids-in-the Mineral Aggregate (Percent), minimum Nominal Maximum Aggregate Size, mm | | | | | Voids Filled w/Asphalt (Percent) | Dust-to-Binder Ratio |
|---|---|---|---|---|---|---|---|---|---|---|
| | $N_{initial}$ | $N_{design}$ | $N_{max}$ | 37.5 | 25.0 | 19.0 | 12.5 | 9.5 | | |
| <0.3 | ≤91.5 | 96.0 | ≤98.0 | 11.0 | 12.0 | 13.0 | 14.0 | 15.0 | 70–80[3] | 0.6–1.2 |
| 0.3 to <3 | ≤90.5 | | | | | | | | 65–78 | |
| 3 to <10 | ≤89.0 | | | | | | | | 65–75[2] | |
| 10 to <30 | | | | | | | | | | |
| ≥30 | | | | | | | | | | |

[1] Design ESALs are the anticipated project traffic level expected on the design lane over a 20-year period. Regardless of the actual design life of the roadway, determine the design ESALs for 20 years, and choose the appropriate $N_{design}$ level.
[2] For 9.5-mm nominal maximum size mixtures, the specified VFA range shall be 73% to 76% for design traffic levels ≥3 million ESALs.
[3] For 25.0-mm nominal maximum size mixtures, the specified lower limit of the VFA shall be 67% for design traffic levels <0.3 million ESALs.
[4] For 37.5-mm nominal maximum size mixtures, the specified lower limit of the VFA shall be 64% for design traffic levels.

SUMMARY OF THE INVENTION

The present invention is a method and apparatus for analyzing bituminous concrete mixes to predict the likelihood of early rutting. The present invention uses a FAT test head that is designed to be used in a gyratory compactor and that takes advantage of the kneading action provided by the gyratory compactor for the purpose of analyzing bituminous mixes to determine whether they are likely to prematurely rut.

According to the present invention, a test specimen of bituminous mix is prepared to a specified air void content and then heated to a constant temperature and then placed in a gyratory compactor. The FAT test head, which consists of a hard rubber block in the shape of a truncated cone mounted in the direct center of a flat, metal circular disk, is placed on top of the specimen in the gyratory compactor with the rubber head down and engaging the test specimen. The gyratory compactor is operated in the normal compaction mode. After the compaction is completed, mix specimen compaction data is analyzed to ascertain the degree of mix deformation for a specified number of gyrations, to thereby predict whether the mix is likely to prematurely rut. Thus, the present invention is useful in determining the best rut resistant aggregate mix when the aggregate is in the aggregate proportioning phase of a volumetric mix design.

The present invention and its advantages will be more completely understood and appreciated by careful study of the following more detailed description of the presently preferred exemplary embodiment of the invention taken in conjunction with the accompanying drawings.

DESCRIPTION OF THE PREFERRED EMBODIMENT

Figure 1:
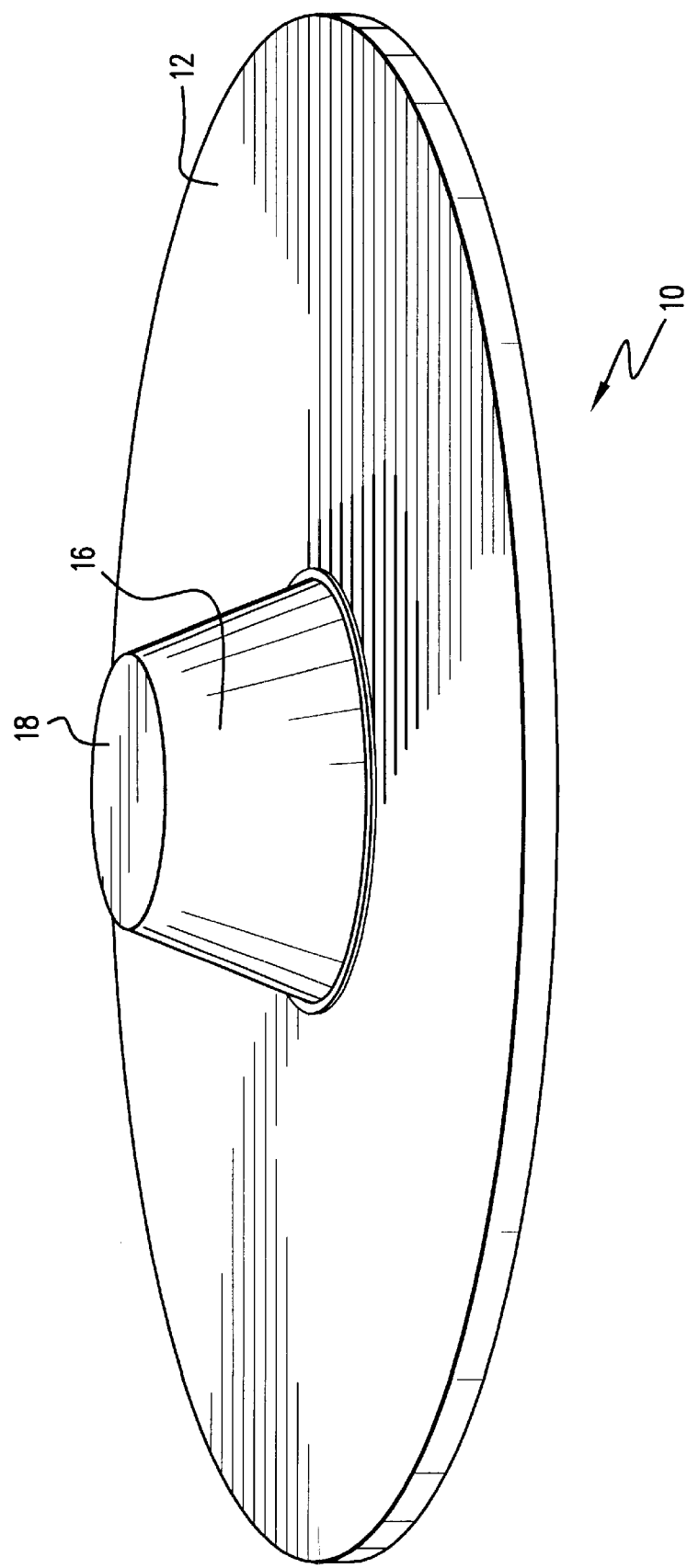
FIG. 1 is a perspective view of the FAT test head of the present invention.
Figure 2:
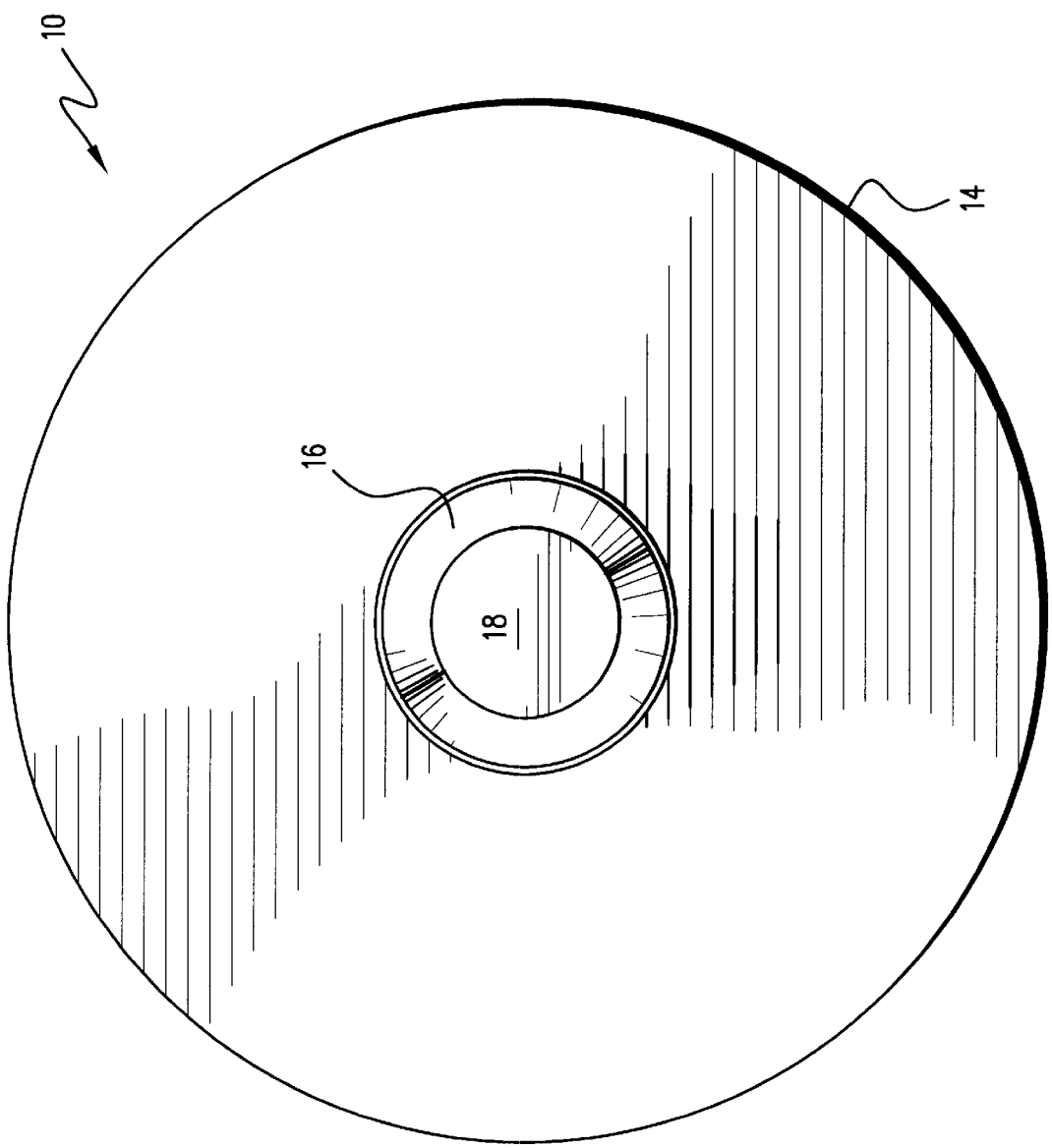
FIG. 2 is a plan view of the FAT test head of the present invention.

The present invention is a method and apparatus for testing mixes of bituminous concrete for the purpose of predicting the likelihood that they will rut prematurely. The present invention uses a FAT test head 10 shown in FIG. 1, FAT is a short name for "Fatigue Tester". The test head 10 includes a flat circular disk 12, which is preferably a steel plate with a thickness 14 that is preferably about six millimeters and a diameter that is preferably about 148 mm. Mounted in the direct center of disk 12 is a hard rubber block 16 in the shape of a truncated cone. Rubber block 16 is preferably a molded EPDM rubber meeting the requirements of ASTM D 2000-M5AA610A13B13C12F17K112-1. Rubber block 16 is also preferably a frustum of a cone, such that it has a flat circular top 18 with a diameter of about 40 mm. The cone 16 preferably has a base diameter of about 60 mm and a height of about 42 mm.

Figure 4:
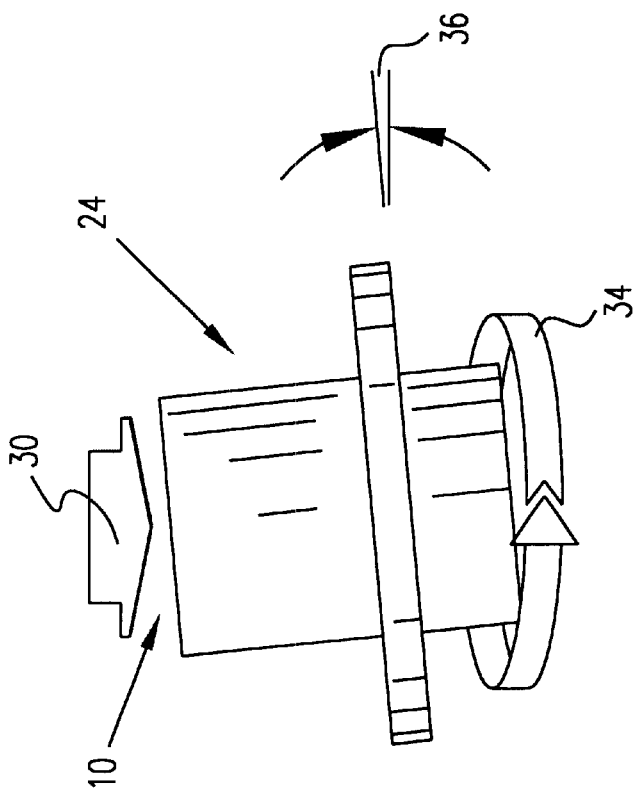
FIG. 4 is a side-elevational view of showing the gyratory motion used by a gyratory compactor to compact specimens of bituminous concrete.
Figure 3:
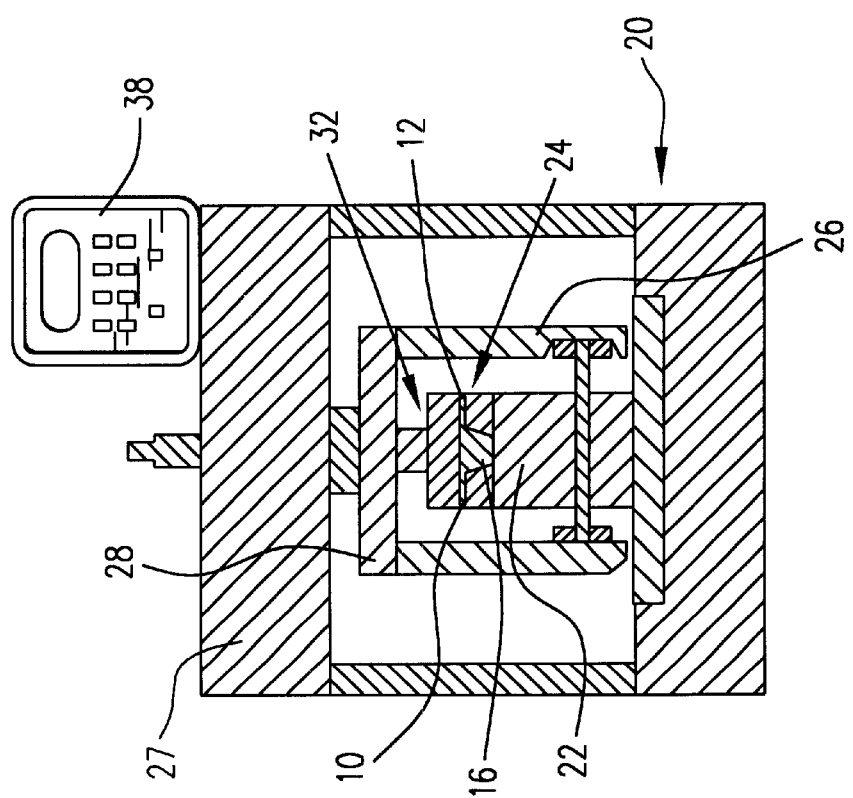
FIG. 3 is a cross-sectional view of a gyratory compactor with the FAT device shown in a mold with a specimen of bituminous concrete.

Test head 10 is intended to be used with a gyratory compactor 20 shown in FIG. 3. Gyratory compactors are well known testing machines used in the design of bituminous concrete mixes. Gyratory compactors use a kneading action, shown in FIG. 4, to compact specimens of bituminous concrete mix. The machines allow for the evaluation of the rate of densification of bituminous mix specimens for the purpose of determining whether the design of the mix is acceptable. Gyratory compactors are available from a number of commercial sources. These include, by way of example, the ITC gyratory compactor made by Interlaken Technology Corporation located in Eden Prairie, Minn., the Troxler gyratory company, Model 4141, made by Troxler Electronic Laboratories, Inc. located in Research Triangle Park, N.C., and the gyratory testing machine made by the Engineering Developments Company, Inc. located in Vicksburg, Miss.

When a bituminous concrete mix is tested in a gyratory compactor 20, a test specimen 22 of the mix is prepared to a specified air void content, and then heated to a constant test temperature and placed in the compactor. Typically, the specimen is heated to a constant test temperature of about 140° F. prior to testing. The air void content is a measure of how many air voids are in the mix. When the mix specimen has been compacted 96%, to be acceptable, preferably the air void content of the mix is in a range between about 4.0 to 2.0. An air void content of less than 2.0 is undesirable.

In operating gyratory compactor 20, a heated mold 24 of a specified diameter is typically loaded with mix specimen 22 and placed in a retaining cylinder 26 located within a reaction frame 27. A gyratory head 28 is then rotated into position and secured, after which hydraulic loading 30 occurs. Typically, a loading Ram 32 is used to exert a pressure on specimen 22. Compaction proceeds at a specified rpm 34 until the specimen 22 reaches a specified height or a specified number of gyrations is reached. Typically, an rpm of 30 gyrations per minute is used for compaction. During the compaction process, vertical pressure is maintained and a specified gyratory angle 36 is maintained. Typically, a Ram pressure of 600 k Pa and an angle of 1.25 degrees are used. Operation of the gyratory compactor is controlled through a control and data acquisition panel 38 connected to compactor 20.

According to the present invention, test specimens of bituminous concrete mix are prepared, heated and tested in a gyratory compactor in a manner that is typical for testing specimen mixes, as described above. However, before operating the compactor, the FAT test head 10 is placed on top of the specimen 22 with the rubber head 16 positioned downward against the specimen 22 within the mold 24, and loaded into mold 24 by means of loading Ram 30. Preferably, the diameter of the flat, metal circular disk 12 is substantially the same as the diameter of the mold 24 into which mix specimen 22 is loaded prior to testing. The gyratory compactor 20 is then operated in the normal compaction mode. After the test is completed, the amount of depth of depression in the height of the specimen mix is analyzed to determine the severity of deformation for the number of gyrations to predict the likelihood of premature compaction of the mix which is manifested as premature rutting.

The present invention will be further illustrated by means of the following examples.

EXAMPLE 1

In the first example, two different specimens of mixes were tested. In Test F2 shown in Table 3 below, the specimen included aggregate with 45% passing #8, while the second specimen in Test F3 included aggregate with 40% passing #8. The passing number 8 is only one portion of the formulation of the tested mix, but it is the easiest sieve size to use in identifying the particular mixes tested.

In Test F2 with the 45% passing #8 specimen, the number of gyrations was varied from 0 to 170. The height of the test specimen and the FAT test head varied from 143 mm at 0 gyrations down to 138.3 mm after 170 gyrations. The amount of depth of depression measured for the specimen varied from 0.0 mm at 0 gyrations down to 4.7 mm after 170 gyrations.

In Test F3 with the 45% passing #8 specimen, again the number of gyrations were varied from 0 to 170, and the height of the test specimen and the FAT test head varied from 143.1 mm at 0 gyrations down to 131.9 mm after 170 gyrations. In this second test the amount of depth of depression varied from 0.0 mm at 0 gyrations down to 11.2 mm after 170 gyrations.

TABLE 3

| | Test F 2 6.0 AC #200 = 4.0 #8 = 40 #4 = 63 3.4 | | | Test F 3 6.0 AC #200 = 4.5 #8 = 45 #4 = 67 3.4 | |
| --- | --- | --- | --- | --- | --- |
| Number of Gyrations | Height of Specimen and FAT Device | Amount of Depth of Depression in mm | Number of Gyrations | Height of Specimen and FAT Device | Amount or Depth of Depression in mm |
| 0.0 | 143.0 | 0.0 | 0.0 | 143.1 | 0.0 |
| 10.0 | 141.8 | −1.2 | 10.0 | 141.3 | −1.8 |
| 20.0 | 141.3 | −1.7 | 20.0 | 140.3 | −2.8 |
| 30.0 | 140.9 | −2.1 | 30.0 | 139.5 | −3.6 |
| 40.0 | 140.6 | −2.4 | 40.0 | 138.7 | −4.4 |
| 50.0 | 140.3 | −2.7 | 50.0 | 138.0 | −5.1 |
| 60.0 | 140.1 | −2.9 | 60.0 | 137.3 | −5.8 |
| 70.0 | 139.9 | −3.1 | 70.0 | 136.5 | −6.6 |
| 80.0 | 139.7 | −3.3 | 80.0 | 135.7 | −7.4 |
| 90.0 | 139.5 | −3.5 | 90.0 | 135.0 | −8.1 |
| 100.0 | 139.3 | −3.7 | 100.0 | 134.4 | −8.7 |
| 110.0 | 139.2 | −3.8 | 110.0 | 134.0 | −9.1 |
| 120.0 | 139.0 | −4.0 | 130.0 | 133.5 | −9.6 |
| 130.0 | 138.9 | −4.1 | 130.0 | 133.2 | −9.9 |
| 140.0 | 138.7 | −4.3 | 140.0 | 132.8 | −10.3 |
| 150.0 | 138.6 | −4.4 | 150.0 | 132.5 | −10.6 |
| 160.0 | 138.5 | −4.5 | 160.0 | 132.2 | −10.9 |
| 170.0 | 138.3 | −4.7 | 170.0 | 131.9 | −11.2 |

In the second set of tests shown in Table 4 below, in Test BB, which again used a test specimen with 40% passing #8, the number of gyrations was again varied from 0 to 170 gyrations. The height of the specimen and the FAT test head varied from 140.6 mm at 0 gyrations down to 135.4 mm after 170 gyrations. The amount of depth of depression varied from 0.0 mm at 0 gyrations down to 5.2 mm after 170 gyrations.

In Test B, which used a 40% passing #8 specimen, again, the number of gyrations was varied from 0 to 170 and the height of the specimen and FAT test device varied from 141.3 mm down to 131.6 mm after 170 gyrations. In this instance, the amount of depth of depression varied from 0.0 mm at 0 gyrations down to 9.7 mm after 170 gyrations.

TABLE 4

| | Test BB 5.5 AC #200 = 4.5 #8 = 40 #4 = 63 Voids = 3.0 | | | Test B 5.5 AC #200 = 3.8 #8 = 35 #4 = 57 Voids = 3.2 | |
| --- | --- | --- | --- | --- | --- |
| Number of Gyrations | Height of Specimen and FAT Device | Amount of Depth of Depression in mm | Number of Gyrations | Height of Specimen and FAT Device | Amount or Depth of Depression in mm |
| 0.0 | 140.6 | 0.0 | 0.0 | 143.1 | 0.0 |
| 10.0 | 139.4 | −1.2 | 10.0 | 139.7 | −1.6 |
| 20.0 | 138.6 | −1.7 | 20.0 | 138.8 | −2.5 |
| 30.0 | 138.3 | −2.0 | 30.0 | 138.1 | −3.2 |
| 40.0 | 130.0 | −2.3 | 40.0 | 137.5 | −3.8 |
| 50.0 | 137.8 | −2.6 | 50.0 | 136.9 | −4.4 |
| 60.0 | 137.5 | −2.8 | 60.0 | 136.4 | −4.9 |
| 70.0 | 137.3 | −3.1 | 70.0 | 135.8 | −5.5 |
| 80.0 | 137.0 | −3.3 | 80.0 | 135.2 | −5.1 |
| 90.0 | 136.8 | −3.6 | 90.0 | 134.7 | −6.6 |
| 100.0 | 136.6 | −3.8 | 100.0 | 134.1 | −7.2 |
| 110.0 | 136.4 | −4.0 | 110.0 | 133.7 | −7.6 |
| 120.0 | 136.2 | −4.2 | 130.0 | 133.2 | −8.1 |

TABLE 4-continued

| | Test BB 5.5 AC<br>#200 = 4.5<br>#8 = 40<br>#4 = 63<br>Voids = 3.0 | | | Test B 5.5 AC<br>#200 = 3.8<br>#8 = 35<br>#4 = 57<br>Voids = 3.2 | |
|---|---|---|---|---|---|
| Number of Gyrations | Height of Specimen and FAT Device | Amount of Depth of Depression in mm | Number of Gyrations | Height of Specimen and FAT Device | Amount or Depth of Depression in mm |
| 130.0 | 136.0 | −4.4 | 130.0 | 132.8 | −8.5 |
| 140.0 | 135.8 | −4.6 | 140.0 | 132.5 | −8.8 |
| 150.0 | 135.6 | −4.8 | 150.0 | 132.2 | −0.1 |
| 160.0 | 135.5 | −5.0 | 160.0 | 131.9 | −9.4 |
| 170.0 | 138.3 | −5.2 | 170.0 | 131.6 | −9.7 |

From the test data shown in Tables 3 and 4, it can be seen that the bituminous pavement formulation containing 40% passing #8 outperformed the formulations containing, in the first test, 40% passing #8, and, in the second test, containing 35% passing #8. The data also show repeatability as to final deformation in both of the formulations with 40% passing #8. In the first Test F2 shown in Table 3, the amount of depth of depression in millimeters was 4.7 mm, and in the second test in Table 4, Test BB, the amount of depth of depression in millimeters was 5.2 mm. The formulation using 40% passing #8 became a final design used on the project for which the testing was done. This formulation was later tested and confirmed appropriate by the Asphalt Institute in Lexington, Ky.

Figure 5:
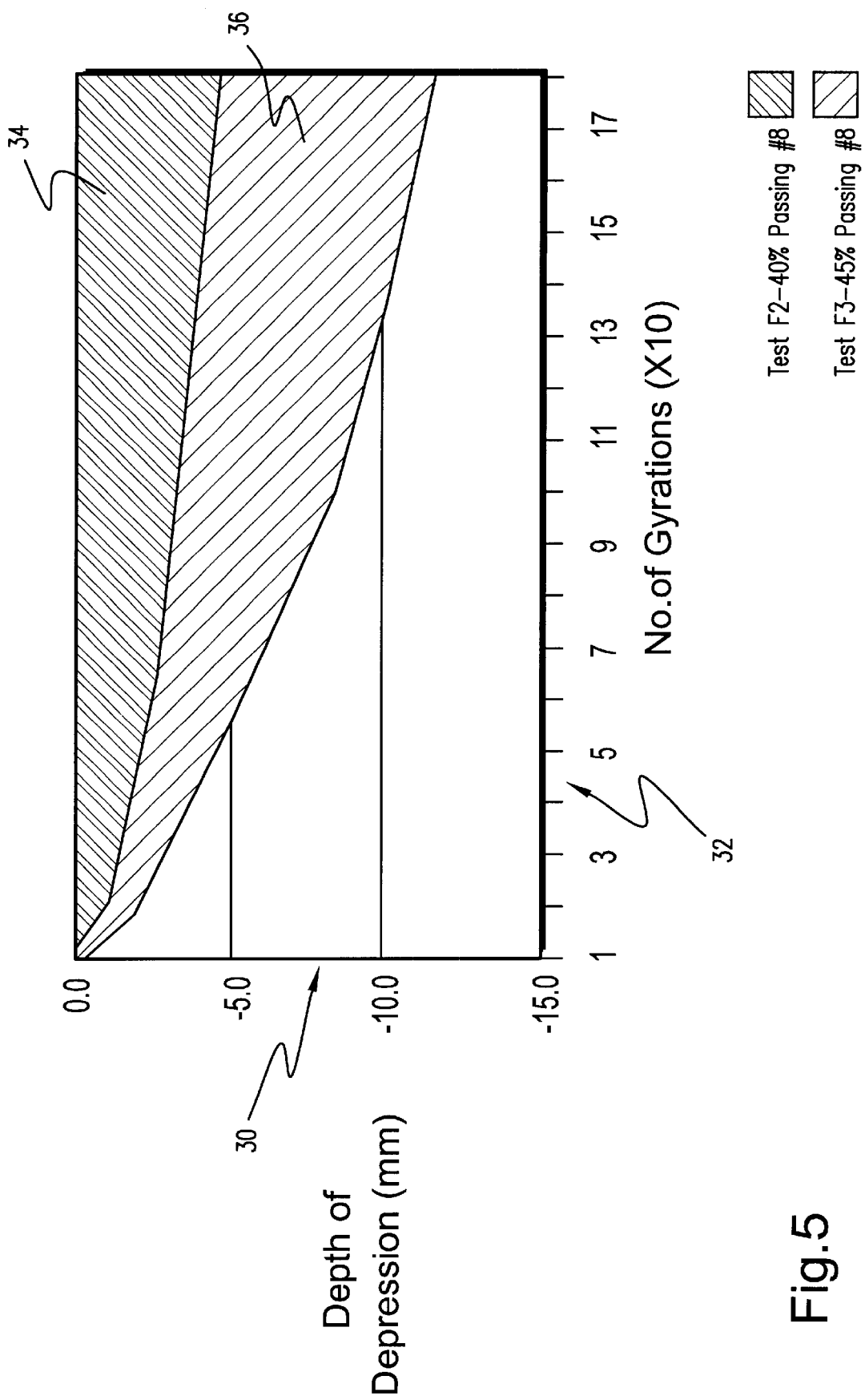
FIG. 5 is a graph of the amount of depth of depression for a given number of gyrations of two bituminous concrete specimens tested according to the present invention.
Figure 6:
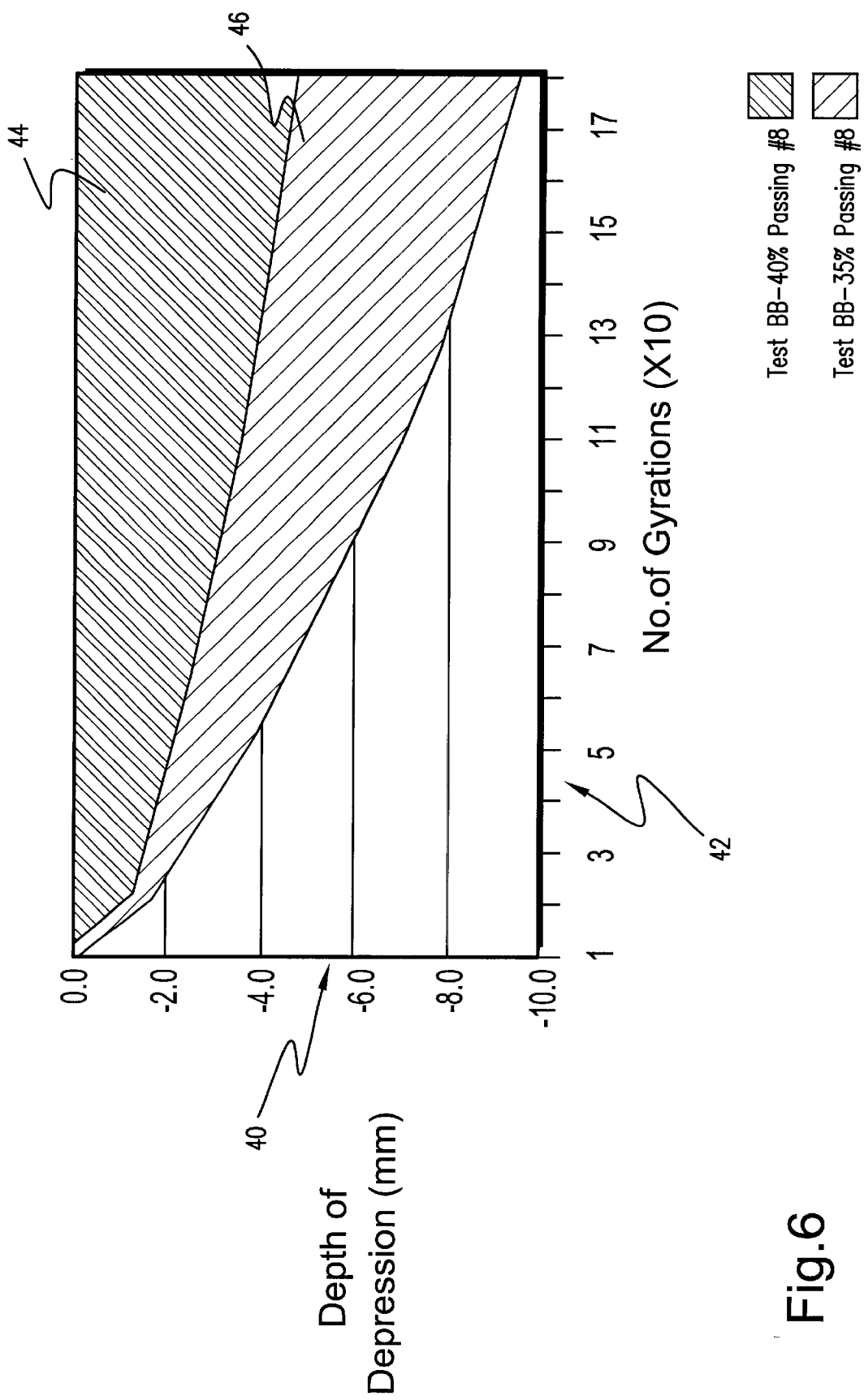
FIG. 6 is a second graph of the amount of depth of depression for a given number of gyrations for two additional specimens of bituminous concrete tested in a gyratory compactor according to the present invention.

The data for the tests shown in Tables 3 and 4 are graphed in FIGS. 5 and 6, respectively. FIG. 5 graphs the test data for the tests F2 and F3 reflected in Table 3. The Y axis 30 of the graph of FIG. 5 shows the amount of depth of depression in millimeters, while the X axis 32 of the graph of FIG. 5 shows the number of gyrations (×10) which resulted in the depth of depression reflected in the graph. The first shading 34 in the graph reflects the specimen with 40% passing #8 in Test F2, while the second shading 36 reflects the specimen with 45% passing #8 used in Test F3.

FIG. 6 graphs the test data for the tests reflected in Table 4. Here again, the graph of FIG. 6 shows the amount of depth of depression in millimeters in the Y axis 40 against the number of gyrations (×10) shown in the X axis 42. The first shading 44 in the graph reflects the specimen with 40% passing #8 used in Test BB, while the second shading 46 reflects the specimen with 35% passing #8 used in Test B.

In all of the tests, the specimens were stabilized at 140° F. prior to testing. The results of the tests can be used to predict that the bituminous mix with 40% passing #8 are less likely to experience the likelihood of premature rutting than the mixes with 45% passing #8 and 35% passing #8. This is demonstrated by the lower amount of depth of depression for the mixes with 40% passing #8 than for the other two mixes.

Although the FAT test head is shown in the preferred embodiment as a flat circular disk with a truncated cone mounted in the direct center of the disk, it should be understood that different geometric shapes or hardnesses can be used for the rubber block. In addition, depending on the rigidity of the specimens being tested, a different range of Ram pressure, or test temperature could be applied. Rigidity of a specimen is evidenced by the stability of a particular mix type, i.e., liquid asphalts for binder containing polymers, etc. which increase the overall strength of a specimen or other additives which may increase overall strength.

The Ram pressure is hydraulically maintained throughout the compaction process, as described above. It may be that Ram pressure may need to be decreased when comparing different types or weaker structure mixes. For example, if a mix deforms completely in a minimal number of gyrations, the pressure may need to be adjusted to better compare similar blends. This decreased pressure would then be used for comparing several variations of that particular mix.

The temperature may be varied if mixes are being designed for a geological area where considerably higher or lower maximum weather conditions occur, e.g., Arizona versus Alaska.

Although the present invention has been described in terms of a particular embodiment, it is not intended that the invention be limited to that embodiment. Modifications of the disclosed embodiment within the spirit of the invention will be apparent to those skilled in the art. The scope of the present invention is defined by the claims that follow.

What is claimed is:

1. A blacktop testing apparatus comprising:
a machine for gyrating and compacting at least one specimen of a blacktop mix;
a separate test head for engaging and compacting said specimen while said specimen is being gyrated by said machine,
said test head including a disk and a block mounted on the disk that engages and compacts said specimen during said machine gyrating of said specimen, and
a device insertable in a depression in a portion of said specimen where said block engages and compacts said specimen during said gyrating of said specimen by said machine for measuring the depth of said depression, said depth of depression being indicative of whether or not said blacktop mix will prematurely rut.

2. An apparatus as recited in claim 1 wherein said disk is substantially circular and said block mounted on the disk is substantially a truncated cone.

3. An Apparatus as recited in claim 2 wherein said disk is metal and said block is rubber.

4. An Apparatus as recited in claim 1 wherein said disk is substantially flat and circular and said block mounted on the disk is substantially a frustum of a cone.

5. An Apparatus as recited in claim 1 wherein said cone is mounted substantially in a center of said disk on one side of said disk.

6. An Apparatus as recited in claim 1 wherein said compacting machine is a gyratory compactor operable on said specimen for predetermined numbers of gyrations.

7. An Apparatus as recited in claim 1 wherein said compacting machine is a gyratory compactor operable on said specimen for predetermined periods of time.

8. An Apparatus as recited in claim 1 wherein said compacting machine is a gyratory compactor operable on said specimen until said specimen was compacted to a predetermined height.

9. An Apparatus as recited in claim 1 wherein said measuring device is a ruler.

10. An Apparatus as recited in claim 11 wherein said measuring device is a ruler.

11. An apparatus for testing blacktop comprising:
a gyratory compactor for gyrating and compacting at least one specimen of a blacktop mix;
a separate test head for engaging and compacting said specimen of blacktop mix while said specimen is being gyrated by said gyratory compactor,
said test head being comprised of a substantially flat, circular disk and a substantially truncated cone shaped block mounted on said disk, said block engaging and compacting said specimen during said gyrating of said specimen in said compactor, and a device insertable in a depression in a portion of said specimen where said block engages said specimen during said gyrating of said specimen in said compactor for measuring the depth of said depression, said depth of depression being indicative of whether or not said blacktop mix will prematurely rut.

12. An Apparatus as recited in claim 11 wherein said disk is metal and said block is rubber.

13. An Apparatus as recited in claim 11 wherein said cone is mounted substantially in a center of said disk on one side of said disk.

14. An Apparatus as recited in claim 11 wherein said gyratory compactor gyrates said specimen for predetermined numbers of gyrations.

15. An Apparatus as recited in claim 11 wherein said gyratory compactor gyrates said specimen for predetermined periods of time.

16. An Apparatus as recited in claim 11 wherein said gyratory compactor gyrates said specimen until said specimen is a predetermined height.

17. A separate test head for testing blacktop fatigue, said test head being insertable with at least one specimen of a blacktop mix in the mold of a gyratory compactor, said test head comprising:

a substantially flat, circular disk shaped to fit into the mold, and a substantially truncated cone shaped block mounted on said disk for engaging and compacting said blacktop mix specimen: during gyrating of said test head and specimen in said gyratory compactor.

18. An Apparatus as recited in claim 17 wherein said disk is metal and said block is rubber.

19. An Apparatus as recited in claim 18 wherein said cone is mounted substantially in a center of said disk on one side of said disk.

20. A method of testing blacktop fatigue comprising the steps of:

preparing at least one specimen of a blacktop mix to a specified air void content, gyrating said specimen in a container for holding the specimen, engaging and compacting said specimen, while said specimen is being gyrated in said container, with a separate test head inserted in the container, the test head including a disk and a block mounted on the disk, and measuring a depth of depression in a portion of said specimen where said test head engages and compacts said specimen during said gyrating of said specimen, said depth of depression being indicative of whether or not said blacktop mix will prematurely rut.

21. A method as recited in claim 20 wherein the step of measuring said depth of depression in said specimen comprises making said measurement where said block mounted on said disk engages and compacts said specimen.

22. A method as recited in claim 20 wherein the step of engaging and compacting said specimen during said gyrating comprises engaging said specimen with a disk that is substantially circular and that has a block mounted on the disk that is substantially a truncated cone.

23. A method as recited in claim 20 wherein the step of engaging and compacting said specimen during said gyrating comprises engaging said specimen with a disk that is metal and block that is rubber.

24. A method as recited in claim 20 wherein the step of compacting said specimen is performed by gyrating said specimen.

25. A method as recited in claim 24 wherein the step of compacting said specimen with said test head is performed for a predetermined number of gyrations.

26. A method as recited in claim 21 wherein the step of compacting said specimen with said test head is performed for a predetermined period of time.

27. A method as recited in claim 21 wherein the step of compacting said specimen with said test head is performed until said specimen is compacted to a predetermined height.

28. A method as recited in claim 21 wherein, in performing the step of measuring said depth of depression in said specimen where said head engages and compacts said specimen, a greater measurement of said depth of depression, is more indicative of said blacktop mix prematurely rutting.

29. A method as recited in claim 28 wherein said measuring step is performed using a ruler.

30. A method as recited in claim 20 wherein said specimen of blacktop mix is heated to a constant specified temperature after said air void content is achieved.

* * * * *